(12) United States Patent
Lafauci et al.

(10) Patent No.: US 7,818,885 B2
(45) Date of Patent: *Oct. 26, 2010

(54) DEVICE FOR PERFORMING SURGERY

(75) Inventors: Michael Lafauci, Center Moriches, NY (US); Scott Berlin, Bayshore, NY (US)

(73) Assignee: Brolex, LLC, West Bayshore, NY (US)

( * ) Notice: Subject to any disclaimer, the term of this patent is extended or adjusted under 35 U.S.C. 154(b) by 352 days.

This patent is subject to a terminal disclaimer.

(21) Appl. No.: 12/025,909

(22) Filed: Feb. 5, 2008

(65) Prior Publication Data

US 2009/0198263 A1 Aug. 6, 2009

(51) Int. Cl.
*B26B 3/00* (2006.01)
(52) U.S. Cl. .......................................... 30/294; 30/280
(58) Field of Classification Search ................... 30/294, 30/2, 340, 280, 289; D8/98, 102
See application file for complete search history.

(56) References Cited

U.S. PATENT DOCUMENTS

| 893,043 | A | | 7/1908 | Westerberg | |
|---|---|---|---|---|---|
| 1,192,748 | A | | 7/1916 | Bundy | |
| 1,577,880 | A | * | 3/1926 | Stuart | 279/93 |
| 2,323,335 | A | | 7/1943 | Kaye | |
| 2,610,399 | A | | 9/1952 | Adams et al. | |
| 2,676,595 | A | | 4/1954 | Dyekjaer | |
| 2,724,178 | A | | 11/1955 | Gensburg | |
| 2,753,105 | A | | 7/1956 | Werner et al. | |
| 3,287,751 | A | | 11/1966 | Hoffman | |
| 3,587,591 | A | | 6/1971 | Satterwhite | |
| 3,624,747 | A | | 11/1971 | McKnight | |
| D230,007 | S | * | 1/1974 | Cramer | D8/98 |
| 3,803,713 | A | | 4/1974 | Jones et al. | |
| 3,835,536 | A | | 9/1974 | Marcoux | |
| 3,877,147 | A | * | 4/1975 | Cummings | 30/329 |
| 4,283,853 | A | | 8/1981 | Fazzini | |
| 4,530,154 | A | | 7/1985 | DiCarlo | |
| D327,125 | S | * | 6/1992 | Iten | D24/146 |
| D332,309 | S | | 1/1993 | Detsch | |
| 5,203,086 | A | * | 4/1993 | Dann | 30/293 |
| 5,285,577 | A | | 2/1994 | Carney et al. | |
| 5,328,026 | A | | 7/1994 | Newman | |
| 5,341,822 | A | * | 8/1994 | Farr et al. | 128/898 |

(Continued)

*Primary Examiner*—Stephen Choi
(74) *Attorney, Agent, or Firm*—Gottlieb, Rackman & Reisman, P.C.

(57) ABSTRACT

A scalpel for performing complex surgeries, such as c-sections, is formed of a body that is preferably elongated and shaped and sized to fit ergonomically into the hands of surgeons. The body has surfaces that are joined to each other by smooth transition elements to insure that the body has no points or sharp edges that could cut or scratch the surgeon or the patient. The body is formed with a triangular notch formed of a beak and an extension. A surgical blade, preferably a standard off-the-shelf surgical blade, is imbedded in the body and the only portion of the blade that is accessible is a portion of its cutting edge spanning the notch. The scalpel is used by introducing the beak into a slit in the tissue with the blade portion facing the direction in which the cut is to be made. The body of the scalpel is then grasped firmly and advanced to make the cut. The initial incision can be made with the tip of the beak.

16 Claims, 6 Drawing Sheets

U.S. PATENT DOCUMENTS

| | | |
|---|---|---|
| D353,316 S | 12/1994 | Schmidt et al. |
| 5,524,348 A | 6/1996 | Tipp |
| 5,555,624 A | 9/1996 | McCracken |
| 5,737,842 A | 4/1998 | Freedman |
| 5,819,419 A | 10/1998 | Schmidt |
| 5,846,250 A | 12/1998 | Parker, III |
| 5,884,837 A | 3/1999 | Jacobsson et al. |
| 5,968,055 A | 10/1999 | Dimitriu |
| 6,102,924 A | 8/2000 | Menzin et al. |
| 6,182,364 B1 | 2/2001 | Reyburn |
| 6,267,774 B1 | 7/2001 | Ishii et al. |
| 6,314,644 B1 | 11/2001 | Raeker |
| 6,409,734 B1 | 6/2002 | Zapata |
| D467,658 S | 12/2002 | Goodwin |
| 6,557,258 B1 | 5/2003 | Roberts et al. |
| 6,619,013 B2 | 9/2003 | Dismukes |
| D481,609 S * | 11/2003 | Perlmutter et al. ............. D8/99 |
| D496,102 S | 9/2004 | Watermeier et al. |
| 6,896,681 B1 | 5/2005 | Watson |
| D514,916 S * | 2/2006 | Craig ......................... D8/102 |
| 2005/0196223 A1* | 9/2005 | Stankovic ................... 401/195 |
| 2006/0016306 A1* | 1/2006 | Conde ........................... 83/13 |
| 2006/0095057 A1 | 5/2006 | Yi et al. |

\* cited by examiner

DEVICE FOR PERFORMING SURGERY

RELATED APPLICATIONS

This application claims priority to U.S. provisional application Ser. No. 60/886,191 filed on Feb. 5, 2007 and incorporated herein by reference.

BACKGROUND OF THE INVENTION

1. Field of the Invention

This invention relates to devices for performing obstetric surgery, and more particularly to a novel device for performing incisions for a caesarian operation, as well as other similar surgical procedures or operations.

2. Description of the Prior Art

Many surgical procedures require one or more incisions to be made in the skin of a patient to provide access to the respective organ requiring active intervention. Additional incisions may be required in the internal tissues as well. For example, a caesarian section (c-section) is started by making an incision at the level of the pubic bone. Additional incisions are made in the walls of the uterus to allow a physician to remove the fetus. At the present, these incisions are made typically with a standard scalpel. However, this accepted technique has been found to be undesirable for several reasons. One reason is that it is hard to control the depth of the cut being made. If the incisions are too deep, they may result in injury to the fetus.

In addition, in the current method a physician uses the blade tip of the scalpel to make the initial cut in the uterine wall and then reverses the scalpel to make an additional puncture. The physician could get injured while he is reversing the scalpel. Moreover, during the actual cutting phase, the physician typically uses his fingers to guide the scalpel along the uterus wall. However, existing scalpels have many sharp edges and points that can injure the physician, the mother or the fetus while the incision is made.

A further disadvantage of existing scalpels is that they are fairly narrow, thin and slippery and ergonomically unfit to hold, especially with a gloved hand, especially after they are covered with body fluids. As a result they are not really suited for operations, such as c-sections, requiring complex and detailed manipulations.

What is needed is a small, light-weight device for performing c-sections or other complex surgeries that can be used safely and effectively by physicians.

SUMMARY OF THE INVENTION

The present invention is a device for performing incisions associated with c-sections and other surgical procedures. It consists of a body which is sized and shaped so that it can be held securely and comfortably by a physician. It includes a body forming a beak used to make an initial puncture in the skin or other membrane. The beak is then inserted into the resulting hole and is advanced, causing the blade to make an incision of a desired length. As the incision is made, a bottom surface of the beak insures an adequate separation between the cutting blade and the underling tissue, thereby preventing undesirable damage to the physician, the mother or the fetus. Preferably, the scalpel is formed of a body having no sharp points or edges and having an ergonomic shape that facilitates different kinds of manipulations. The scalpel can be used for c-sections, laparoscopic procedures, etc.

BRIEF DESCRIPTION OF THE DRAWINGS

FIG. 5b shows a front view of the embodiment of FIG. 5a;

FIG. 5c shows a top view of the embodiment of FIG. 5a;

FIG. 6a shows a side view of a third alternate embodiment of the invention;

FIG. 6b shows a front view of the embodiment of FIG. 6a;

FIG. 6c shows a top view of the embodiment of FIG. 6a;

FIG. 6d shows an enlarged top view of the beak area of the embodiment of FIG. 6a;

FIG. 6e shows an enlarged front view of the beak area of the embodiment of FIG. 6a;

FIG. 6j is a partial orthogonal view of the beak of the embodiment of FIG. 6a;

DETAILED DESCRIPTION OF THE PREFERRED EMBODIMENT

Figure 1:
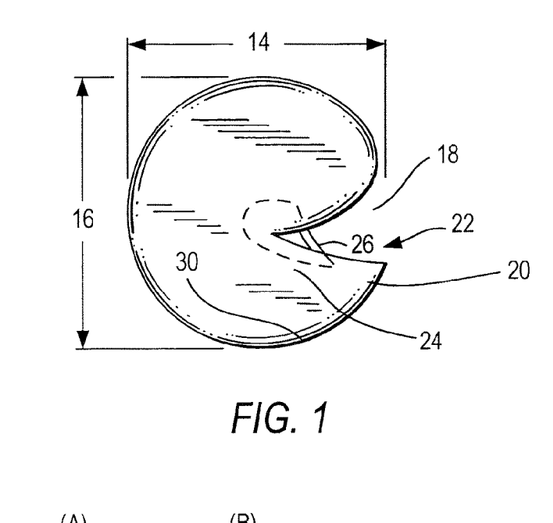
FIG. 1 is a side view of one embodiment of the cutting device constructed in accordance with this invention.
Figure 2:
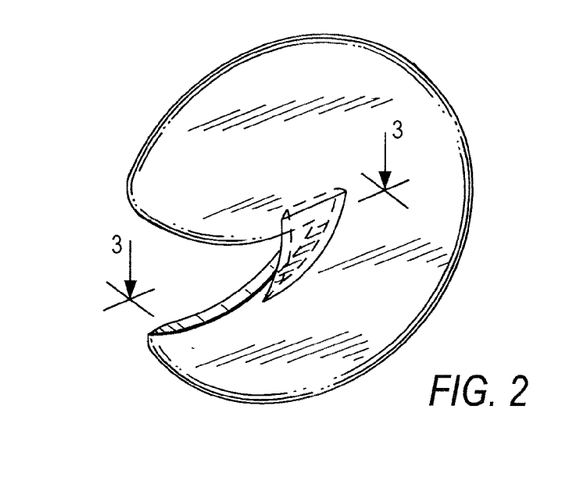
FIG. 2 is a perspective view of the cutting device of FIG. 1.
Figure 3:
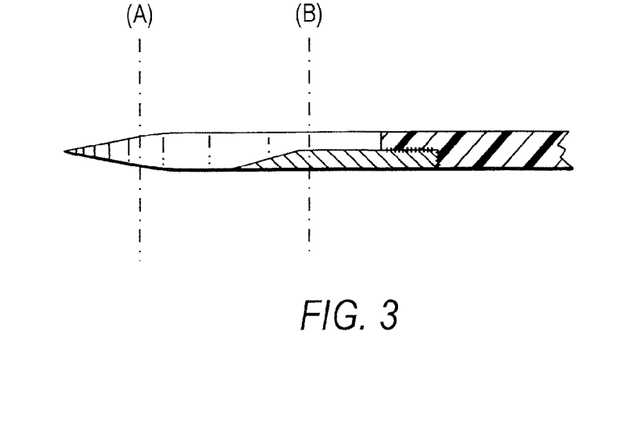
FIG. 3 is a cross-sectional view along line 3-3 of the cutting device of FIG. 2.

Referring first to FIGS. 1-3, a device 10 for performing incisions for a c-section includes a generally oval body 12 having a width 14 and a height 16 of about 50-80 mm and a thickness of about 3-6 mm. Other dimensions and shapes are suitable as well, as long as the device is light and comfortable to hold. The body is made with a triangular notch 18 forming a beak 20. The beak 20 is terminated with a rounded point 22. The notch holds a cutting blade 24 formed with a sharp edge 26.

The device 10 is used as follows. First, the tissue is punctured with the point 22. The beak 20 is then inserted through the resulting hole and advanced until the lateral side of the hole (not shown) is reached by the edge 26. The device is then advanced causing the edge 26 to make a clean incision of the desired length. While the skin or other membrane (e.g., the uterus) is being cut during this process, a lower surface 30 of the beak 20 separates the tissues of the organ or the fetus disposed immediately beneath and insures that a minimum spacing is maintained, thereby preventing any incidental damage. To ensure that device 10 cannot cut the physician, mother or fetus, surface 30 is either round or flat. Moreover, the size and shape of the device insures that a physician does not prick or cut himself during surgery.

The device can be made from a single solid material. However, it is preferably to have the body 12 made of a suitable plastic material that is easy to make, using well known molding or other techniques, and is easy to sterilize. The cutting blade can be made of surgical steel or other similar materials and can be either imbedded in the body 12 during molding or can be attached later.

Figure 4:
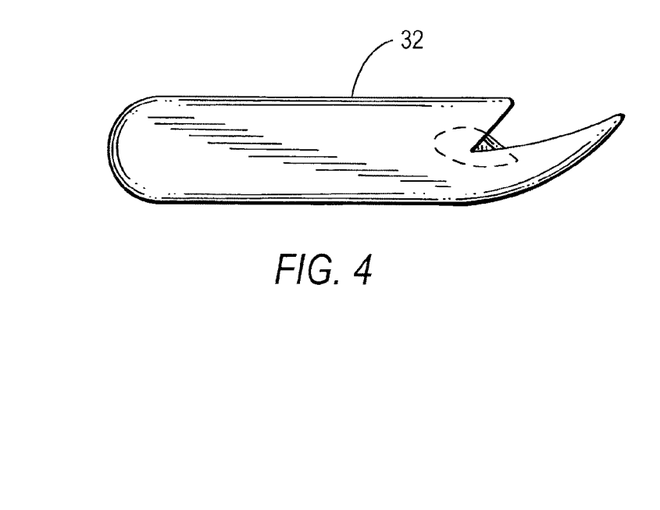
FIG. 4 is a side view of a first alternate embodiment of the invention.

In FIG. 4, an alternate device 32 is shown with an elongated body. This shape may be preferred by some physicians because it is similar to a traditional scalpel and therefore may look more familiar.

Figure 5A:
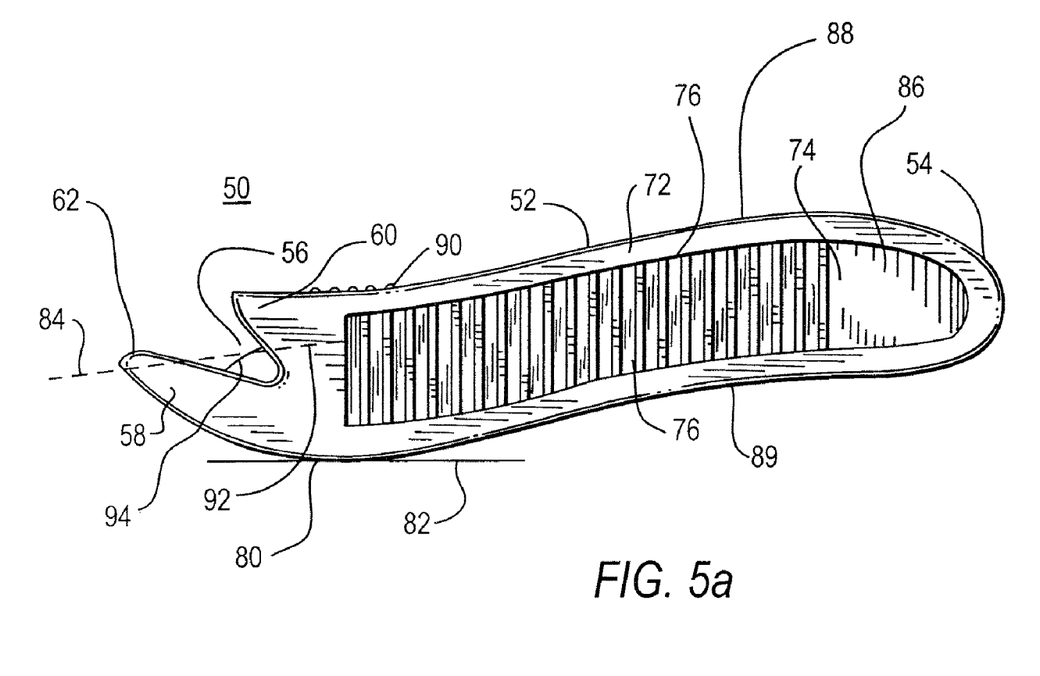
FIG. 5a shows a side view of a second alternate embodiment of the invention.
Figure 5B:
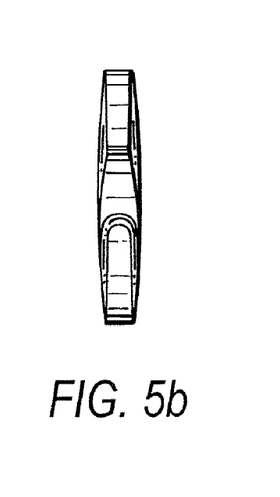
Figure 5C:
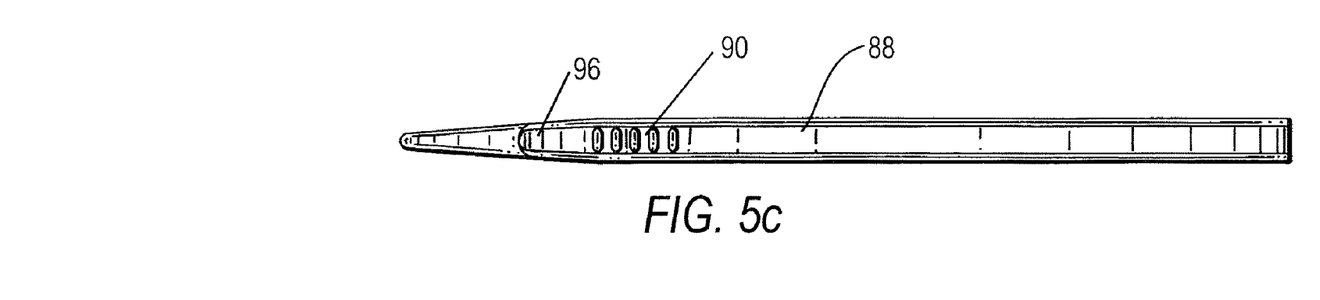

Studies were conducted with several physicians to ergonomically optimize the shape, size and configuration of the scalpel. Two such configurations are described below. FIGS. 5a-5c shows one such embodiment. In this embodiment, scalpel 50 an elongated curved body 52 that is rounded at one end 54 and a triangular notch 56 at the other end. The notch 56 is formed between the beak 58 and an extension 60. Beak 58 terminates in a rounded point 62. As seen in FIG. 5b, the beak 58 has a triangular cross-section thicker at the bottom than the top. This novel shape insures that the point 62 is strong and does not deflect when used to apply pressure and pierce a tissue or membrane of the patient as discussed above. The extension 60 is shorter then the beak 58 to provide good viewing angles of the blade and of the portion of tissue being cut.

The body 52 has two identical lateral surfaces, one such surface 70 being visible in FIG. 5a. This surface is formed with a peripheral rim 72 separated from a central depression 74 by a rounded ledge or rail 76. This rounded ledge or rail 76 can be used to easily grasp, push or pull the scalpel 50. Prior art scalpels do not possess any such features.

The central depression 74 is formed with a plurality of parallel vertical ridges 78. As seen in FIG. 5a, when the scalpel 50 is oriented so that its lowest point 80 is tangential to an imaginary horizontal surface 82, the ridges 78 are perpendicular to the horizontal surface 82. When the scalpel is used, the imaginary surface 82 is parallel to the tissue 84 being cut. Therefore, the ridges 78 provide the physician with an indication of how the scalpel 50 is oriented with respect to the tissue 84.

Preferably near the rounded end 54, the depression 74 has a flat or blank area 86 that can be used to provide a logo, a model number, etc.

Scalpel 50 has a top edge 88 that is formed near extension 60 with several protrusions 90. The protrusions 90 provide more friction when the physician has to apply pressure on edge 88 with a finger during a procedure. The top edge 88 and the bottom edge 89 form longitudinal edges for the scalpel 50 and are curved to provide the scalpel with a body that is easy to grasp. The curvature of the edges and the protrusions 90 provide the physician with a clear indication of the correct orientation for the scalpel 50 during surgery.

An important part of the scalpel 50 is blade 92. Preferably the body 52 is molded from a plastic material over the blade 92 and therefore in FIG. 5a only a portion 94 of the cutting edge of the blade is visible. This portion 94 can be straight, convex or concave. Returning to FIG. 5c, near its forward end, the edge 88 is formed with a knife indication 96 in the form of a line or depression corresponding to the position of the portion 94. Therefore the indication 96 assists the physician in determining the exact position of the cutting edge portion 94.

Preferably, the body 52 has an overall length of about 3-5", and more particularly between 4.800-5.00", because range can accommodate physicians with hands in the range of 6-8". The width of the body can range between 0.800-1.000" and a thickness of between 0.150 and 0.250". The present inventors have found that a scalpel having a body of about 4.82" in length, a width at point 80 of 0.916" and a maximum thickness of 0.200" is particularly advantageous.

FIGS. 6a-6j display another embodiment of the invention similar to the one in FIGS. 5a-5c. In the embodiment just described, the inventive device has a somewhat uniform width, except at the forward end. In this latter embodiment, the scalpel 100 is tapered so that it is wider near the rounded end 102 and then near the notch 104. The scalpel 100 is also thicker. The preferred dimensions of the scalpel 100 are 4.863"×0.916" (at point 124)×0.250". Thus, overall this latter embodiment provides a heftier feel. Moreover, the extended width results in longer grooves 106 to accommodate hands of different sizes as well as more positions for the hands on the scalpel 100.

Figures 6A, 6B:
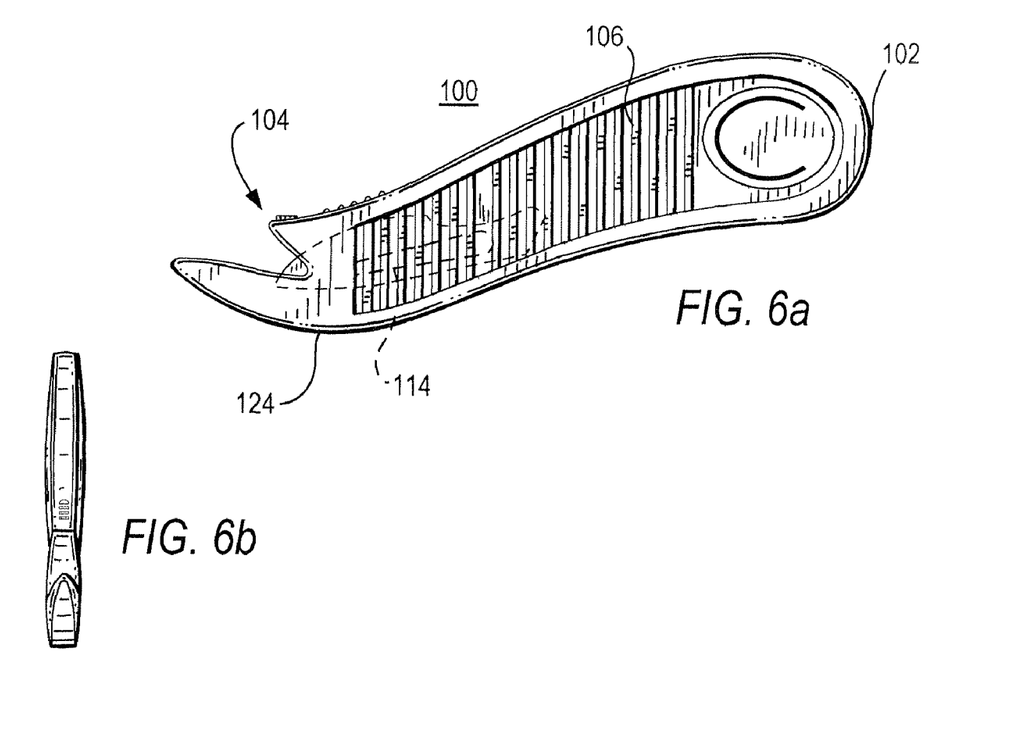
Figure 6C:
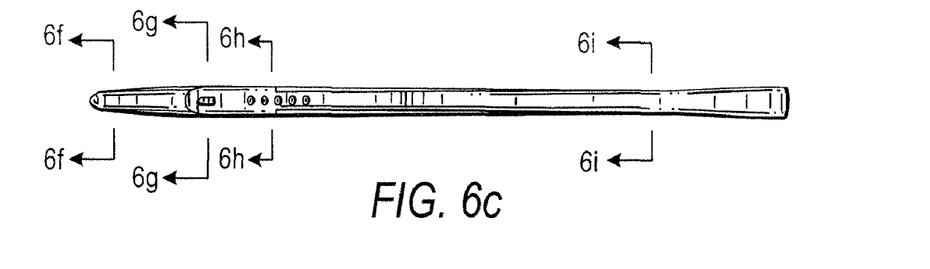
Figure 6D:
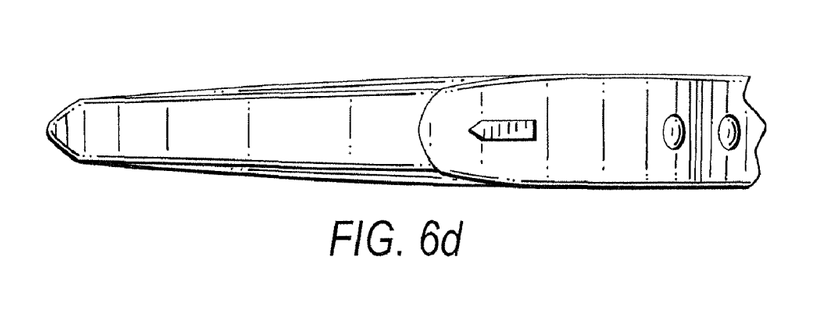
Figures 6E, 6J:
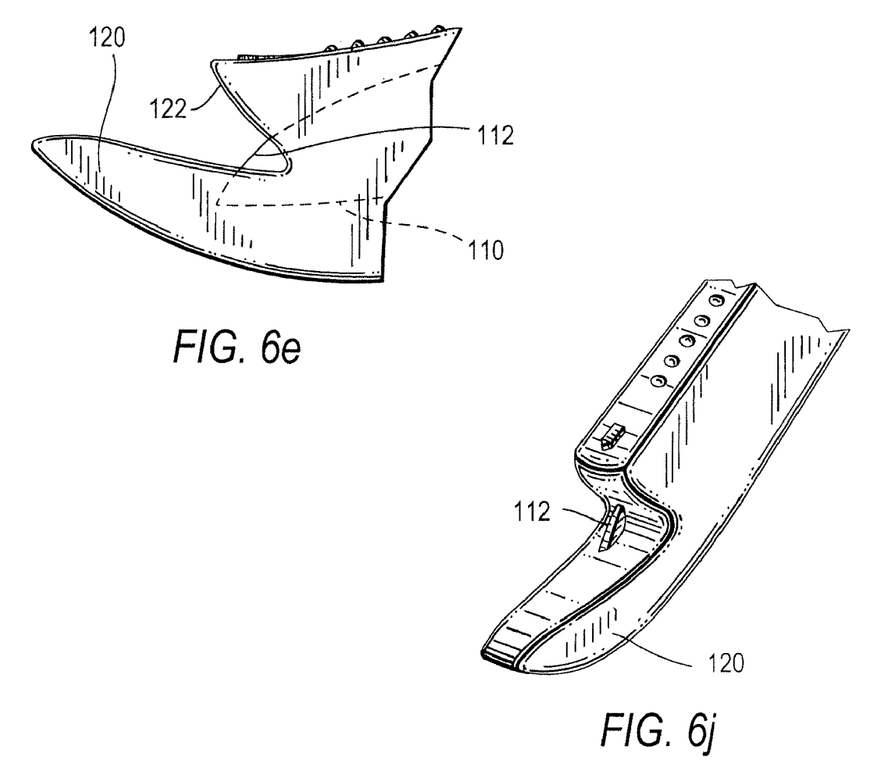
Figure 6F:
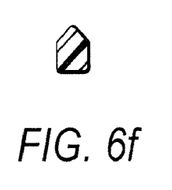
FIGS. 6f-6i are cross-sectional views taken along lines A-A, B-B, C-C, D-D respectively in FIG. 6c.
Figure 6G:
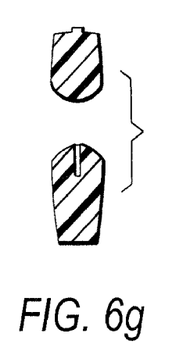
Figure 6H:
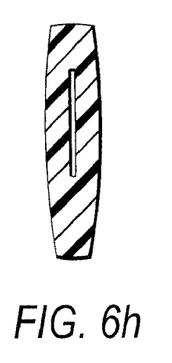
Figure 6I:
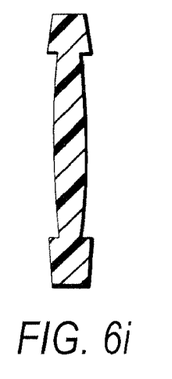

FIG. 6a also shows the outline of the blade 110 with its visible cutting edge portion 112. Preferably blade 110 is a standard surgical blade that is readily available from numerous sources. In the figure, blade 110 is a No. 23 blade with an elongated cutout 114. Other blades can be used as well. Alternatively, a custom designed blade may be used. Of course, such a blade may increase the cost of the scalpel.

Figure 7A:
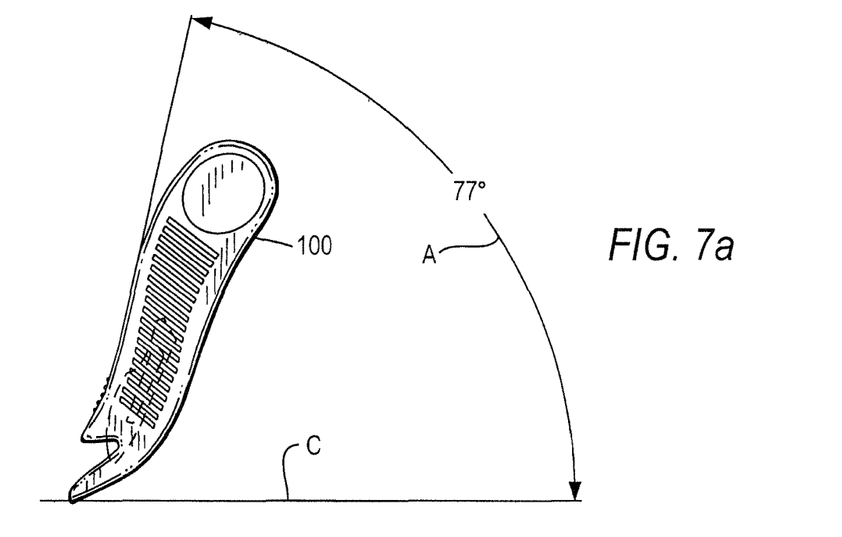
FIG. 7a shows a front view of the embodiment of FIG. 6a in a first position used to make the initial puncture for a surgery operation.
Figure 7B:
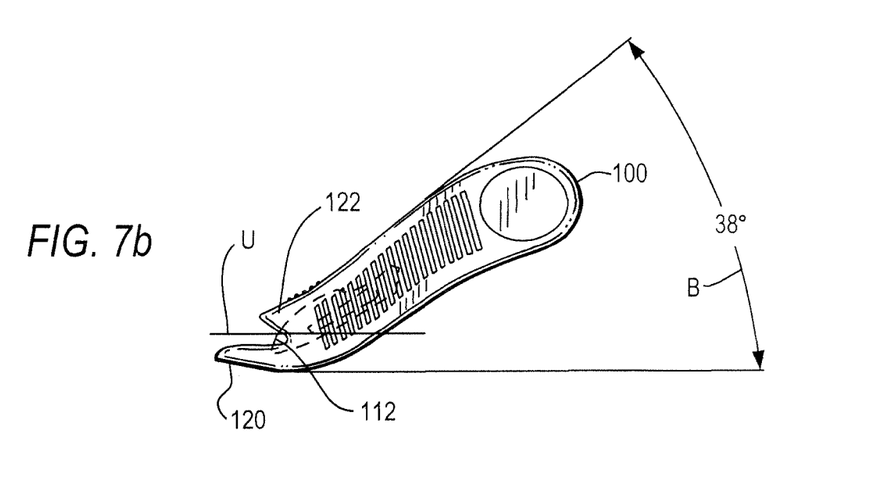
FIG. 7b shows a front view of the embodiment of FIG. 6a in a second position for starting the cut in the wall of the uterus.
Figure 7C:
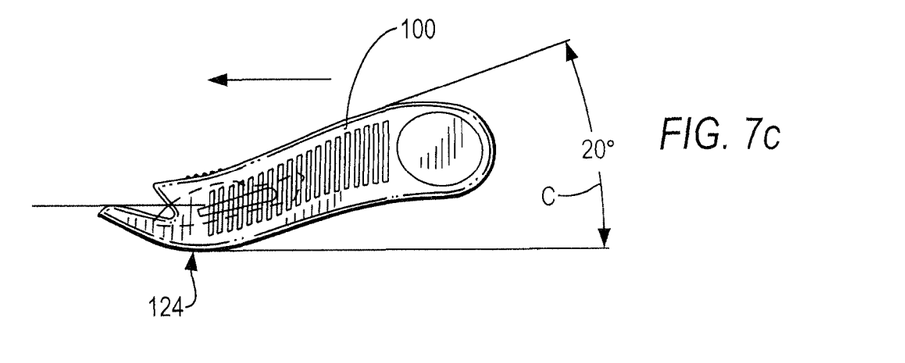
FIG. 7c shows a front view of the embodiment of FIG. 6a in a third position for actual making the cut.
Figure 7D:
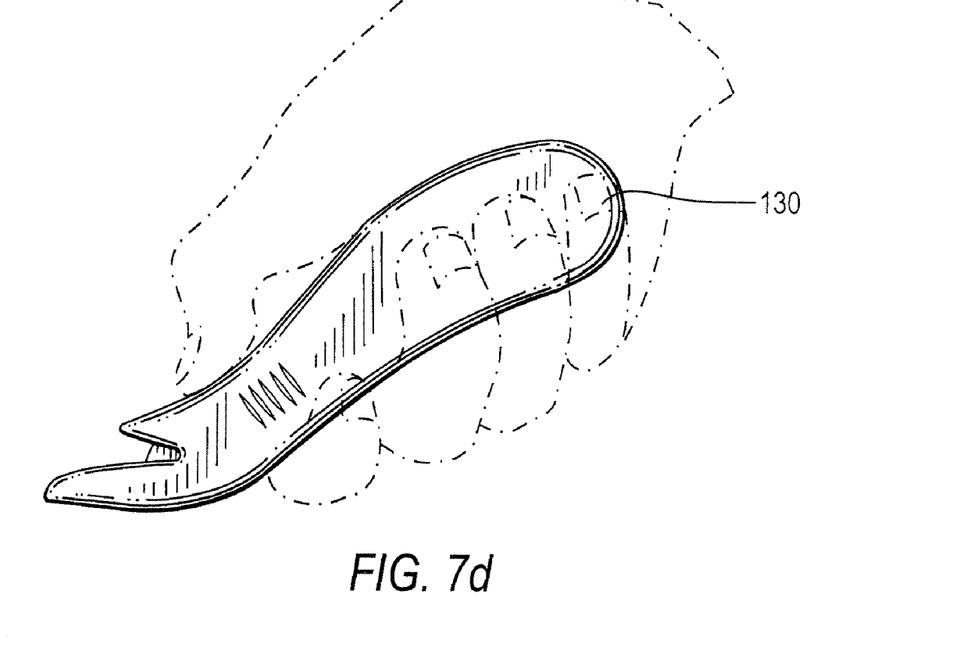
FIG. 7d shows the scalpel in the position of FIG. 7c further indicating the fingers of the physician.

FIGS. 7a-7c illustrate how the embodiments of FIGS. 5a-c and 6a-d may be used to perform a c-section. In FIG. 7a the physician positions a scalpel (e.g. 100) as shown. The angle A may be in the range of 75-80 degrees and preferably about 77 degrees. The scalpel is used in this position to puncture the wall of the uterus U. If the wall is too thick, the physician may cut a small (1") opening therein with a standard scalpel. The beak 120 is then positioned under the wall U at an angle B in the range of 35-40 degrees and preferably 38 degrees. The scalpel 100 is designed so that it is comfortable to hold in this position. Because the extension 122 is shorter then the beak 122, the cutting edge 112 is visible to the physician from the top. The physician then rotates the scalpel 100 until it reaches an angle C of about 15-25 degrees and preferably 20 degrees, and starts advancing the scalpel. In this position, the beak 120 pushes the wall U slightly upward and ready to be cut by the edge 112. While this motion is continued, the sharp edge 112 cuts the wall U smoothly and the point 124 insures that the scalpel passes smoothly over the fetus and that the fetus is not injured. FIG. 7d shows the scalpel of FIG. 6c in the hands of the physician. The circles, e.g. circle 130, indicate the position of the physician's fingers during this step.

As discussed above, the body of the scalpel is overmolded on the standard surgical blade from a suitable plastic material. Except for the cutting edge of the blade, the body is formed with surfaces that are joined with rounded transitions with a nominal radius of about 0.030" to insure that it presents no sharp edges or points. In this manner, the scalpel prevents injuring and infecting the physician, the patient and the fetus. The body can be provided in colors different from those of other instruments or in particular colors for different hospitals and departments to avoid confusion. The body can also be made of, or include, a compound visible by x-rays so that after the surgery is completed, the patient can be x-rayed to insure that the scalpel has not been left in the patient inadvertently. The device is made preferably of relatively cheap materials so that its manufacturing costs are reduced and so that it can be discarded, either after each use, or after each procedure.

Figure 8:
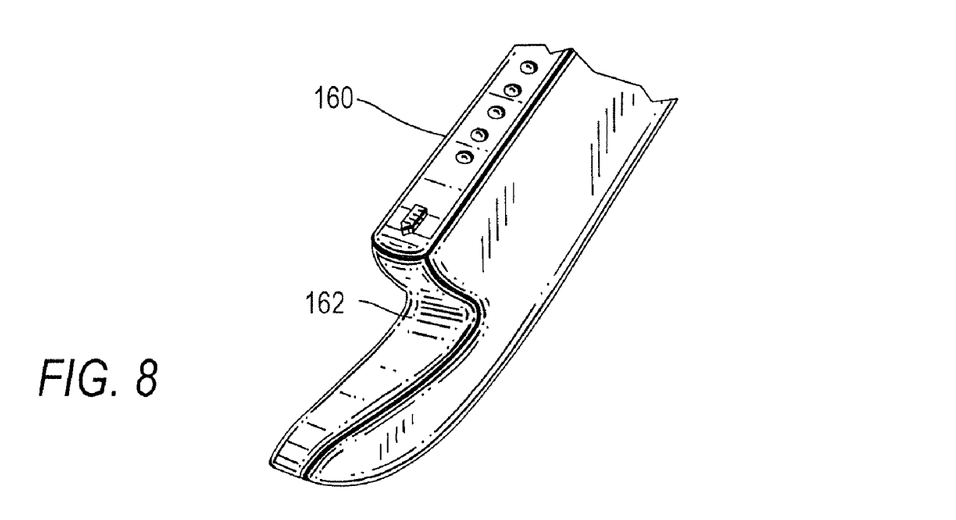
FIG. 8 shows a partial orthogonal view of another embodiment of the invention.

Another embodiment of the invention is shown in FIG. 8. In this embodiment a scalpel is shown having a body 160 similar to the ones in FIG. 5 or 6; however it does not have an imbedded steel blade. Instead, the base notch is shaped so that a plastic blade 162 is formed between the extension 164 and the beak 166. The blade has to be hard enough to be able to cut tissues, just as described above. The blade 162 is made integrally with the body 160 in a single molding operation.

In summary, the present invention presents a disposable surgical scalpel, such as an obstetrical scalpel, which aids in safer c-section deliveries by reducing knife injuries made from scalpel blades. Manufactured from a strong, break resistant plastic material, such as Lexan®, with a surgical blade embedded within, the scalpel provides enough resistance to pierce through the last tissues of uterine and amniotic tissue and cleanly cut across the uterus without lacerating the baby. Briefly, in the context of Caesarean section delivery, the factors that need to be taken into consideration when designing such a scalpel are: safety, performance, intuitiveness, and construction. The present scalpel has been designed with these factors in mind, as illustrated below. As a result, these factors provide a framework that renders the surgical scalpel very useful and unique.

Safety:
1. No knife lacerations made on baby due to unique piercing tip and embedded blade for a quick, clean incision.
2. Intuitive hand position increasing grip and control, decreases mis-use.
3. Clear sight lines over cutting edge.
4. Grip provides close proximity to blade to avoid loss of control while cutting.
5. Iconic shape, easily identifiable on the tool field.
6. Arrives to the Operating Room sterile, packaged, ready for surgery
7. Disposable post surgery Performance:
1. Grip utilizes all fingers to increase control
2. Unique handle and blade configuration that pushes through the tissue like a scissor.
3. Ribbing perpendicular to cutting path increases grip.
4. Unique handle shape allows surgeon to back off or move up on tool, thereby increasing control and sight lines to cutting path.
5. Unique round edged tip will pierce through layers of tissue
6. Specific hand and tool position increase control and accuracy of incision.
7. Embedded surgical blade creates clean path through uterine tissues.
8. Increased sight-lines over cutting edge will decrease chance of vascular injury to mother.

Intuitiveness:
1. Iconic shape will not be confused for something else on the surgical tool field.
2. Grip discourages a downward piercing action, or an "ice pick" action due to it's unique grip and intuitive hand position
3. Tool can only be held two ways, pinched or grasped.
4. Clear sight lines provide a safe range of movement and motion through the uterine tissue.
5. Unique "jaw" opening provides visual description of approximate tissue cutting depth.
6. Identifiable shape, won't be confused with another tool.

Construction:
1. Economical use of materials
2. Blade inserted into tool and cast into plastic C-Safe handle
3. Innovative break-resistant plastic
4. X-Ray opaque if lost of broken during surgery.

Numerous modifications may be made to this invention without departing from its scope as defined in the appended claims.

We claim:

1. A surgical scalpel configured to perform a C-section on a patient with a uterus outer wall having a uterus surface, said scalpel comprising:

an elongated flat body shaped to fit comfortably in the hand of a surgeon and having two opposed flat surfaces defining generally a thickness for the body, two opposed longitudinal edges including a top longitudinal body edge extending along a top tangential line and a bottom longitudinal body edge, said longitudinal body edges having respective first and second ends, a round end joining the first ends of said longitudinal body edges, and a notch disposed at the second ends of said longitudinal body edges, said notch being formed between an extension, a beak and a cutting blade spanning said extension and said beak;

said extension having a top extension edge formed by the second end of said top body edge and an extension lower edge extending downwardly at an acute angle from said top longitudinal edge;

said beak terminating in a piercing point extending further then said extension, said beak having a top beak edge extending linearly backwardly to said extension lower edge, and a lower beak edge with a curved shape extending from said piercing point to the end of said lower body edge, said top beak edge being disposed at an angle of about 35-40 degrees with respect to said top tangential line;

said body being configured to be positioned by the surgeon successively to three positions during a C-section procedure including:

a) a first position for piercing the uterus outer wall with said piercing point, in said first position, said body being positioned with said top tangential line is disposed at an angle of about 75-80 degrees with respect to the outer wall of the uterus, in said first position, said body being configured to pierce the outer wall of the uterus with said piercing point of said beak;

b) a second position for starting to make an incision in the uterus wall, in said second position, the body being positioned with the beak disposed under the uterus wall with beak upper edge disposed in parallel with the uterus surface and the tangential wall being disposed at an angle of about 35-40 degrees with respect to the uterus surface and said top beak edge; and c) a third position in which the piercing point is pushing the uterus wall upward to direct to position it for a clean cut as the body is moved in said third position along the uterus surface, with the top tangential wall being disposed at an angle of about 15-25 degrees with respect to a bottom tangential line, said bottom tangential line being tangential to said beak bottom surface and parallel to the uterus wall.

2. The scalpel of claim 1 wherein said longitudinal edges define a substantially constant width for the body.

3. The scalpel of claim 1 further comprising grooves on said surfaces.

4. The scalpel of claim 1 wherein said longitudinal bottom edge has a bottom point disposed near said beak, wherein said grooves are perpendicular to a line tangential to said bottom point.

5. The scalpel of claim 1 wherein said surfaces are provided with grasping elements to allow the scalpel to be grasped during a surgery.

6. The scalpel of claim 5 further comprising a rim disposed around at least one of said flat surfaces, said rim being joined to said surface by a ledge.

7. The scalpel of claim 1 wherein said top longitudinal edge, includes protrusions near said extension.

8. The scalpel of claim 1 wherein one of said longitudinal edges has a marking aligned with said cutting portion to provide an indication of the position of said cutting portion.

9. The scalpel of claim 1 wherein body is defined by a plurality of surfaces, said surfaces being joined by rounded transitions to eliminate any sharp edges and points on said body.

10. The scalpel of claim 1 further comprising a surgical blade made of a metallic material and embedded in said body, said blade having a cutting edge having a cutting portion that is exposed and spans said notch.

11. The scalpel of claim 10 wherein said blade is a standard surgical blade.

12. The scalpel of claim 1 wherein said cutting blade is formed integrally as a thinned portion of the body, said body and blade being made of a plastic material.

13. The scalpel of claim 1 wherein said extension is shorter than said beak and said top longitudinal edge is aligned to provide a clear line of sight to said blade as viewed from the top along said top tangential line .

14. The scalpel of claim 1 wherein said beak has a triangular cross-section that is wider at the bottom than at the top supporting the blade, said beak terminating in a rounded point.

15. The scalpel of claim 1 wherein said edges are rounded so that they have no edge surfaces with radii of curvature of less than 0.030".

16. The scalpel of claim 1 wherein said cutting blade is made of surgical steel with a cutting edge extending between an upper point on said lower extension edge and a lower point on said top beak edge, said upper and lower points being spaced from the intersection between said lower extension edge and said top beak edge.

* * * * *

UNITED STATES PATENT AND TRADEMARK OFFICE
CERTIFICATE OF CORRECTION

| | |
|---|---|
| PATENT NO. | : 7,818,885 B2 |
| APPLICATION NO. | : 12/025909 |
| DATED | : October 26, 2010 |
| INVENTOR(S) | : Michael Lafauci and Scott Berlin |

It is certified that error appears in the above-identified patent and that said Letters Patent is hereby corrected as shown below:

IN THE SPECIFICATION:

At column 1, line 2, please change "S.N. 60/886,191" to --Serial No. 60/888,191--

Signed and Sealed this
Eighth Day of September, 2015

Michelle K. Lee
*Director of the United States Patent and Trademark Office*